United States Patent [19]

Kawai et al.

[11] Patent Number: 4,794,081

[45] Date of Patent: Dec. 27, 1988

[54] PROCESS FOR THE PREPARATION OF RIBOFLAVIN

[75] Inventors: Kimitoshi Kawai; Akinobu Matsuyama, both of Himeji; Shoichi Takao, Sapporo, all of Japan

[73] Assignee: Daicel Chemical Industries, Ltd., Sakai, Japan

[21] Appl. No.: 643,226

[22] Filed: Aug. 21, 1984

[30] Foreign Application Priority Data

Sep. 9, 1983 [JP] Japan ................... 58-165245
May 17, 1984 [JP] Japan ................... 59-99096
May 17, 1984 [JP] Japan ................... 59-99097

[51] Int. Cl.$^4$ .................. C12P 25/00; C12N 1/16
[52] U.S. Cl. ............................ 435/66; 435/85; 435/255; 435/256; 435/119
[58] Field of Search .............. 435/85, 86, 66, 119 146, 435/255, 942, 256; 514/675; 426/62, 56; 424/93, 127, 195.1

[56] References Cited

U.S. PATENT DOCUMENTS 4,118,512 10/1978 Eichelburg ..................... 424/359
4,310,635 1/1982 Hasegawa et al. ............... 435/146

OTHER PUBLICATIONS

Giri et al., "Studies on the Synthesis of Riboflavin by a Mutant Yeast, *Saccharomyces cerevisiae*" *J. Bact.*, vol. 67 (1954) pp. 309–313.
Gross et al., "Identification of Mutants Defective in the First and Second Steps of De Novo Protein Synthesis in *S. cerevisiae*" Biochimica et Biophysica Acta 247(1971) pp. 13–21.
Bacher et al., "The Structure of Purine Precursor in Riboflavin Biosynthesis" *Angew. Chem. Internat. Edit.*, vol. 8 (1969) No. 5, pp. 371–372.
Hilton, J. L., "Inhibitions of Growth and Metabolism by 3-Aminotriazole (Amitrole)" *J. Agr. Food Chem.* 17(2) Mar.–Apr. 1969.

Klopotowski, T. "Adaptation of Yeast to 3-Amino-1,2,4-Triazole" *Acta Biochim. Polon.*, 10:199–208, 1963.
Klopotowski et al., "Partial Reversal by Purine and Pyrimidine Bases of Yeast Growth Inhibition Produced by 3-Amino-1,2,4-Triazole" *Acta Biochim. Polon.*, 13: 153–163 (1966).
Hilton, J. L., "Modes of Action of 3-Amino-1,2,4-Triazole: Current Status" Isotope Weed Research Proc. Symp. Vienna (1965) pp. 71–83.
Riboflavin Biosynthesis by *Candida robusta*, Parts 1 and 2; by Shoichi Takao, Agr. Biol. Chem., vol. 28, No. 8, pp. 559–565, 1964.
Nutritional Growth Requirements for *Butyribacterium methylotrophicum* on Single Carbon Substrates and Glucose by Thomas T. Moench and J. G. Zeikus; Current Microbiology, vol. 9, pp. 151–154, 1983.

*Primary Examiner*—Charles F. Warren
*Assistant Examiner*—Irene Marx
*Attorney, Agent, or Firm*—Flynn, Thiel, Boutell & Tanis

[57] ABSTRACT

Riboflavin is obtained directly from the culture in a high yield by cultivating a riboflavin-producing microorganism in a medium using a lower ($C_1$ to $C_4$) aliphatic compound, separating riboflavin contained in the culture in the form of heated aqueous solution from solid matters, and crystallizing riboflavin from the heated aqueous solution.

Riboflavin is also prepared in a high yield by cultivating a riboflavin-producing yeast belonging to the genus Saccharomyces which has purine requirements and/or resistance to 3-amino-1,2,4-triazole in a medium and collecting riboflavin formed and accumulated in the medium.

Moreover, riboflavin is prepared in a high yield even in the presence of iron ions by preliminarily cultivating in liquid a riboflavin-producing yeast belonging to the genus Saccharomyces and then cultivating it in a riboflavin-producing medium containing zinc ions.

11 Claims, No Drawings

PROCESS FOR THE PREPARATION OF RIBOFLAVIN

BACKGROUND OF THE INVENTION

1. Field of the Invention

The present invention relates to a process for the preparation of riboflavin by fermentation.

Riboflavin can be prepared in a high yield by the fermentation method according to the present invention, using acetic acid as carbon source. The present invention further relates to a process for obtaining riboflavin formed by fermentation as crystals from the culture. Riboflavin is of value for the applications as medicine and food-stuff additives or colorants for food.

2. Description of the Prior Art

Typical riboflavin-producing microorganisms known at present are Ascomycetes such as *Ashbya gossypii* or *Eremothecium ashbyii*, with which riboflavin for food-stuff is industrially prepared from saccharides for the production of additives for food-stuff.

It is known that riboflavin is produced not only by Ascomycetes but also by some bacteria belonging to the genus Clostridium or yeasts of the genus Candida, Saccharomyces, or Hansenula (see Progress in Industrial Microbiology, Vol. 1, p. 139 (1959)). However, the productivity of riboflavin is low when bacteria or yeasts are used and it is also noticed that the presence of iron ions in trace amounts greatly decreases the productivity. Because of these disadvantages, the production of riboflavin with bacteria or yeasts has not yet been put into industrial practice (see Annual Review of Microbiology, Vol. 26, p. 369 (1972)).

Some of the present inventors reported on a process for the preparation of riboflavin by fermentation using acetic acid as a carbon source (see Takao, Agr. Biol. Chem, Vol. 28, pp. 559, 566 & 765 (1964)).

As to the recovery of riboflavin out of the culture, riboflavin for food-stuff additives is obtained by drying the entire culture without isolation of riboflavin. In that case, a method of utilizing the difference in specific gravity is suggested in order to obtain as high a riboflavin concentration as possible (see Japanese Patent Laid-Open No. 159800/1980).

Highly purified crystalline riboflavin, which can be used for medicaments and the like, has been obtained by heating the culture to solubilize riboflavin, separating insoluble matters comprising microorganisms from the solution, and thereafter separating riboflavin from that solution by temporarily changing riboflavin into a less soluble form (Economic Microbiology, Vo. 2, p. 315, Academic Press).

An example of this method is described in detail in Japan Patent Publication No. 10155/1978, according to which riboflavin is converted into reduced-form riboflavin having low solubility by the addition of a hydrosulfite and precipitated as crude crystals. The obtained crystals are oxidized in an acidic suspension and purified by recrystallization. Purified riboflavin can be prepared by this method, but the yields were too low for practical use. According to Example 1 of Japan Patent Publication No. 13276/1982, the heated culture solution from which bacteria have been removed is concentrated and reduced with titanium trichloride to form a precipitate. The precipitate is oxidized in air and purified by dissolution in hydrochloric acid and alkali precipitation (29% yield after purification). It is also known to extract the product using butanol or other organic solvents in the treatment of reduced-form (leuco) riboflavin (U.S. Pat. No. 2,464,243).

SUMMARY OF THE INVENTION

Although it has been known that riboflavin can be recrystallized from water, oxidized-form riboflavin contained in the culture has been purposely converted into the reduced form with a reducing agent and then re-oxidized for purification, because it has been difficult to directly crystallize highly purified riboflavin from the culture, unlike the case of recrystallization from pure water. It is known that the solubility of riboflavin in water is greatly dependent on the presence of organic nitrogen compounds or other substances. It is assumed therefore that a variety of substances contained in a substance like molasses, most ordinarily used as a substrate for fermentation, have prevented highly purified riboflavin crystals from being obtained.

The first object of the present invention is to provide a process by which riboflavin crystals can be obtained by simple crystallization from an aqueous culture solution, which has not been put into industrial practice so far, by overcoming of the above-described disadvantages.

As mentioned above, although a variety of riboflavin-producing microorganisms are known, there are still many problems to be solved for the materialization of industrial preparation of riboflavin by fermentation, among which, the discovery of a microorganism with which riboflavin can be obtained with high accumulation concentration and production rate is most important.

From this point of view, the second object of the present invention is to provide a novel process for the preparation of riboflavin using a strain having high riboflavin-productivity.

The third object of the present invention is to provide an improved process for the cultivation of riboflavin producing yeast preserved on an agar medium, said yeast being preliminarily cultivated in a liquid medium, by which the productivity of riboflavin is remarkably improved and the inhibition by iron ions is prevented.

The embodiment of the invention to accomplish the first object comprises a process for the preparation of riboflavin by cultivating a microorganism having riboflavin-producing ability in a culture medium and collecting riboflavin formed and accumulated in the culture, characterized by conducting cultivation on a culture substrate of a lower aliphatic ($C_1$–$C_4$) compound, separating riboflavin contained in the culture in the form of a heated aqueous solution from solid matter and crystallizing riboflavin from said heated aqueous solution.

The embodiment of the invention to accomplish the second object comprises a process for the preparation of riboflavin, characterized by cultivating in a culture medium a riboflavin-producing yeast belonging to the genus Saccharomyces and having purine requirements and/or resistance to 3-amino-1,2,4-triazole to form and accumulate riboflavin therein, and collecting the accumulated riboflavin.

The embodiment of the invention to accomplish the third object comprises a process for the preparation of riboflavin, characterized by planting a yeast belonging to the genus Saccharomyces and having riboflavin-producing ability, after pre-cultivation in liquid, on a riboflavin-producing culture medium containing zinc ions.

DETAILED DESCRIPTION OF THE INVENTION

In the first embodiment, lower aliphatic ($C_1$–$C_4$) compounds such as lower aliphatic acids, lower aliphatic alcohols, lower aldehydes, esters, or acetals are used as substrate. The use of these compound, represented by acetic acid, methanol, ethanol, butanol, or glycerol, leads to the easy preparation of highly purified riboflavin crystals, unlike the conventional methods, by the simple crystallization of the product from the aqueous solution of the culture. Lower aliphatic compounds are advantageous in that they have small molecular weights and simple structures, can be easily purified by, for example, distillation, and are suitable for use in the form free from impurities that affect the crystallization.

In order to prepare riboflavin by cultivation using a lower aliphatic compound as a substrate, it is necessary to use a microorganism suitable for the purpose. The strain disclosed in the literature by some of the present inventors relating to a process for the preparation of riboflavin by fermentation using acetic acid as carbon source (see Agr. Biol. Chem. Vol. 28, pp. 559, 566 & 765 (1964)) is one of the examples. The microorganism was designated in said literature as *Candida robusta*, but as spores were found in the type strain of *Candida robusta* later, *Candida robusta* is re-classified as *Saccharomyces cerevisiae* in J. Lodder's *The Yeast* (1970).

However, as no formation of spores was recognized in the strain discussed in said literature, it is assumed that the strain is a non-spore type of *Saccharomyces cerevisiae*. The strain is hereinafter referred to as *Saccharomyces cereviciae* (*Candida robusta*) in the present specification.

Other appropriate strains for the first embodiment include, for example, mutants derived from *Saccharomyces cerevisiae* (*Candida robusta* AHU 3405), which characterize the second embodiment.

One of the microorganisms used in the second embodiment is a riboflavin-producing fungus belonging to the genus Saccharomyces and having purine requirements. Any microorganism that has these characteristics can be used. What distinguishes the present microorganism from those employed in the prior art is the purine requirement. An example of the appropriate strains is *Saccharomyces cerevisiae* P-154 (FERM BP-566), which is a purine-requiring mutant derived from *Saccharomyces cerevisiae* (*Candida robusta* AHU 3405). The strain of *Saccharomyces cerevisiae* P-154 can be relatively easily obtained by subjecting a parent strain of a riboflavin-producing yeast belonging to the genus Saccharomyces to ordinary mutation treatment.

More particularly, *Saccharomyces cerevisiae* (*Candida robusta* AHU 3405) (listed as one of the preserved microorganisms of the Faculty of Agriculture, Hokkaido Univ.), selected as parent strain, is irradiated with ultraviolet ray or treated with an agent such as N-methyl-N'-nitro-N-nitrosoguanidine and then smeared on a yeast extract-malt agar medium. The desired mutant is selected from the grown colonies by the following method: the replica of said colonies is formed on a culture medium containing the minimum medium having the composition shown in Table 1 and 0.005% of a purine compound such as adenine, and such colony is the selected as a purine-requiring mutant that cannot be grown in the minimum medium but can be grown in the medium containing a purine compound.

TABLE 1

| Composition of Minimum Medium | |
|---|---|
| Ingredient | Concentration |
| glucose | 20 g/l |
| $(NH_4)_2SO_4$ | 2 g/l |
| $MgSO_4.7H_2O$ | 0.5 g/l |
| $KH_2PO_4$ | 1.5 g/l |
| biotin | 2 μg/l |
| agar | 15 g/l |
| pH | 6.0 |

The growth test of the obtained mutant on purine compounds was conducted to examine the purine requirements of the mutant according to the following method. *Saccharomyces cerevisiae* (*Candida robusta* AHU 3405), the parent strain, and the mutant derived therefrom were cultivated for 24 hours in a nutritious liquid medium having the composition shown in Table 2, and washed with physiological saline. The suspensions of the cultures were each inoculated on 5 ml portions of the minimum medium to which various amounts of purines shown in Table 3 had been added. After the cultivation was continued for 3 days at 30° C., the growth rate of the strains was measured based on the absorbance at 610 nm. The relative growth rate of the mutant, with the growth rate of the parent strain being 100, is shown in Table 3. The minimum medium to which purine compounds in amounts listed in Table 3 had been added had the same composition as shown in Table 1 except that agar and biotin were omitted and that 103 g/l of calcium acetate were added in place of glucose.

It is confirmed from Table 3 that *Saccharomyces cerevisiae* P-154 was endowed with purine requirements.

TABLE 2

| Nutritious Liquid Medium | |
|---|---|
| Ingredient | Concentration |
| glucose | 20 g/l |
| yeast extract | 3 g/l |
| malt extract | 3 g/l |
| polypeptone | 5 g/l |
| pH | 6.0 |

TABLE 3

| | Relative Growth Rate | |
|---|---|---|
| Strain | Purine concn. (%) | Relative growth rate |
| *Saccharomyces cerevisiae* (*Candida robusta* AHU 3405) | 0 | 100 |
| | adenine 0.1 | 100 |
| *Saccharomyces cerevisiae* P-154 | 0 | 0 |
| | adenine 0.01 | 129 |
| | adenine 0.1 | 94 |
| | hypoxanthine 0.1 | 94 |

Other microorganisms used in the second embodiment include any riboflavin-producing yeast belonging to the genus Saccharomyces and having resistance to 3-amino-1,2,4-triazole. They are distinguished from those employed in the prior art in the resistance to 3-amino-1,2,4-triazole. *Saccharomyces cerevisiae* TW-573 (FERM BP-567), and *Saccharomyces cerevisiae* TP-1010 (FERM BP-565), which are 3-amino-1,2,4-triazole-resistant mutants derived from *Saccharomyces cerevisiae* (*Candida robusta* AHU 3405) and *Saccharomyces cerevisiae* P-154 (FERM BP-566), respectively, are the examples of the strains suitable for the second embodiment.

These strains can be obtained relatively easily by subjecting parent strains of riboflavin-producing yeast belonging to the genus Saccharomyces to ordinary mutation treatment.

More particularly, the same parent strain as that shown in the example of the preparation of the purine-requiring mutant is subjected to the same mutation treatment and then smeared on the agar medium having the composition shown in Table 1 and further containing $CaCl_2 \cdot 2H_2O$ (0.3 g/l) and 3-amino-1,2,4-triazole in an amount which prevents the growth of the parent strain. The grown colony is selected as 3-amino-1,2,4-triazole-resistant mutant.

When the parent strain requires nutrients, the ingredients required are further added to the medium having the above-described composition, and thereafter the 3-amino-1,2,4-triazole-resistant mutant can be selected in the same manner as above.

The growth test of the obtained mutants on 3-amino-1,2,4-triazole was conducted to examine the resistance to 3-amino-1,2,4-triazole of the mutants, according to the following method: the parent strain and the 3-amino-1,2,4-triazole-resistant mutants were washed with physiological saline and the suspensions of the strains were each inoculated in 5 ml portions of the medium listed in Table 1, to which 3-amino-1,2,4-triazole in amounts listed in Table 4 had been added. After the cultivation was continued for 2 days at 30° C., the growth rate of the strains was measured based on the absorbance at 610 nm. The relative growth rate of the strains, with the growth rate of the strains to which no 3-amino-1,2,4-triazole was added being 100, is shown in Table 4. The culture medium having the composition of Table 1 to which 0.005% of adenine had further been added was used for *Saccharomyces cerevisiae* P-154 and *Saccharomyces cerevisiae* TP-1010 derived therefrom.

TABLE 4

| Strain | Relative Growth Rate 3-Amino-1,2,4-triazole concn. (mM) | Relative growth rate |
| --- | --- | --- |
| Saccharomyces cerevisiae (Candida robusta AHU3405) | 0 | 100 |
| | 1 | 1 |
| | 5 | 0 |
| | 10 | 0 |
| Saccharomyces cerevisiae TW-573 | 0 | 100 |
| | 1 | 60 |
| | 5 | 19 |
| | 10 | 1 |
| Saccharomyces cerevisiae P-154 | 0 | 100 |
| | 20 | 22 |
| | 40 | 20 |
| | 80 | 20 |
| | 100 | 9 |
| Saccharomyces cerevisiae TP-1010 | 0 | 100 |
| | 20 | 111 |
| | 40 | 92 |
| | 80 | 49 |
| | 100 | 17 |

It is confirmed from Table 4 that *Saccharomyces cerevisiae* TW-573 and *Saccharomyces cerevisiae* TP-1010 are endowed with the resistance to 3-amino-1,2,4-triazole.

For the first embodiment, the preferred microorganism is the one that requires relatively small amounts of nutrients, produces riboflavin without addition of meat extract, polypeptone, corn steep liquor or other substances having a complicated composition, and does not produce large amounts of by-products other than riboflavin, to avoid large amounts of substances affecting the crystallization of riboflavin. The microorganisms described above satisfy these conditions, too.

The culture in which riboflavin is formed with the substrate, medium ingredients, and the microorganism selected according to the standard described above has a less complicated composition than those of the prior art, thus making it possible to prepare more purified riboflavin crystals in higher yields, followed by the separation of the solid matters such as yeast cells or calcium carbonate from the heated aqueous solution, and the crystallization of the product from the aqueous solution by cooling or other ordinary method.

The culture from which the crystals are to be separated may be in a state of liquid obtained after fermentation (broth) or of solid matter obtained by cooling and filtering or centrifuging the solution after fermentation, in which yeast cells and riboflavin crystals are mixed. As at least part of the formed riboflavin is considered to be embedded in the cells, it must be extracted with hot water, and separated together with those existing outside the cells in the form of a heated aqueous solution from yeast cells and other solid matters. The conditions for the extraction with water are determined considering the stability and solubility of riboflavin. Usually, the extraction is carried out under acidic conditions at a temperature not lower than 50° C., preferably not lower than 60° C. Water, for example, at 120° C. can be used under pressure. The amount of the water must be sufficient for dissolving the riboflavin contained in the culture and varies according to the temperature of the heated aqueous solution. Therefore, water is usually added not only when solid matters are used but also when the culture solution itself is used.

Although riboflavin crystals are obtained when the heated aqueous solution is simply cooled, the liquid extract may be optionally concentrated (while separating calcium carbonate or the like, if formed) and then crystallized.

Riboflavin crystals having higher purity can be obtained by optional recrystallization using water, aqueous acetic or hydrochloric acid solution, or other solvents.

A process for the cultivation of a riboflavin-producing microorganism on a lower aliphatic compound as carbon source will now be described according to the first embodiment. Nitrogen compounds in various forms can be used as nitrogen source. Inorganic nitrogen compounds are preferred and they include, for example, ammonium sulfate, ammonium chloride, and ammonium carbonate. The use of large amounts of polypeptone, or other organic nitrogen sources may adversely affect the crystallization.

Potassium dihydrogen phosphate, magnesium sulfate, or other inorganic salts are further incorporated besides said carbon and nitrogen sources. When purine-requiring strains are used, purine compounds such as adenine, mineral acid salts of adenine, adenosine, adenylic acid, ribonucleic acid, and further hypoxanthine, inosine and the like are added. Moreover, optional incorporation of vitamins such as biotin, micronutrients such as amino acids or nucleic acid bases may increase the amount of riboflavin accumulated.

Aerobic conditions are preferred for the cultivation. The pH value of the culture medium is from 2 to 10, preferably from 6 to 9 for most desirable results. The temperature is from the range of 20° to 37° C. considering the appropriateness for the growth of the stains used and for the production of riboflavin.

The cultivation method described above is applicable to the cultivation of mutants in the second embodiment. Carbon and nitrogen sources can be selected from among a broader range in the second embodiment, including glucose, sucrose, xylose, and other saccharides, or amino acids, polypeptone, and other organic nitrogen compounds. When these compounds are used, however, riboflavin must be prepared by a method other than that of the first embodiment.

In the report mentioned in the foregoing paragraph (Takao, 1964), riboflavin was prepared by directly inoculating a yeast preserved on an agar medium to a riboflavin-producing medium. The effect of metal ions was then examined by the addition of 0.1 mg/l, 1 mg/l, and 5 mg/l portions of various metal ions. As the result, Bi, Li, and Mn ions were found to be a little effective, while Fe, Ag, Cu, and Hg ions were found to prevent the preparation of riboflavin.

It was reported that zinc-containing samples showed the same values as those to which the metal had not been added (12.1 to 12.8 mg/100 ml). The present inventors, however, unexpectedly found that the addition of a trace amount of zinc to a medium for the production of riboflavin, in which a yeast grown on an agar medium was to be inoculated, not directly but after pre-cultivation in a liquid medium, remarkably improved the productivity of riboflavin, and also decreased the adverse effect due to iron ions, which leads to the accomplishment of the third embodiment.

In more detail, the third embodiment comprises inoculating a riboflavin-producing yeast grown on an agar medium, for example, *Saccharomyces cerevisiae* (*Candida robusta* AHU 3402) or *Saccharomyces cerevisiae* (*Candida robusta* AHU 3405) on a liquid medium for pre-cultivation, which contains glucose, yeast extract, polypeptone, and the like, cultivating the yeast under shaking for 1 to 2 days at 30° C., and then the yeast has been grown sufficiently, inoculating a predetermined amount of the preculture on a riboflavin-producing medium directly or after washing with physiological saline.

It is preferable to inoculate the pre-culture solution to the riboflavin-producing medium in an amount of 3% or more. The greater amount of the inoculated pre-culture brings about the higher riboflavin productivity. For example, when 3.8% of the pre-culture was inoculated to a medium containing 0.5 mg/l of zinc, 0.92 g/l of riboflavin was obtained after 6 day cultivation, while when 2.5% of the pre-culture was inoculated, riboflavin was obtained in an unsatisfactory yield of 0.38 g/l.

However, inoculating in too large amounts is also disadvantageous. The amount of the inoculated pre-culture is preferred to be 25% or less. The carbon and nitrogen sources in the third invention are the same in the second invention.

Zinc ions can be added in the form of zinc sulfate, chloride, or acetate. The concentration of the zinc ions to be added may be determined on scrutinizing the effect, but the preferable amount of the zinc ions may be within the range of 0.2 to 100 mg/l. Small amounts of 0.05 mg/l or less are not effective, while too large amounts, for example, exceeding 300 mg/l of zinc ions are not preferable because the growth of the yeast and the utilization rate of the carbon source are considerably decreased.

The most desirable concentration of the zinc ions is varied in dependence on the concentration of the iron ions contained in the medium. For example, when the amount of iron ions is 0.1 mg/l or less, 0.5 mg/l of zinc ions will suffice. However, when 5 mg/l of iron ions are contained, it is necessary to add 10 to 30 mg/l of zinc ions.

Requisites for the cultivation, such as temperature, pH, and the necessity for keeping aerobic conditions, are the same as in the first and second inventions. Shaking culture, submerged aeration-agitation culture, or other methods are employed in the third invention.

The present invention will be more readily understood by the following examples. The microorganisms used in the examples were pre-cultivated under the following conditions and then inoculated in the fermentation medium in an amount of 12.6%.

Pre-cultivation conditions:
inoculated in 100 ml of a pre-culture medium containing:
2% glucose,
0.5% polypeptone,
0.3% yeast extract, and
0.3% malt extract
shaking cultivation at 30° C. for 30 hours.

Fundamental composition of fermentation medium:

| | |
|---|---|
| calcium acetate | 103 g/l |
| $(NH_4)_2SO$ | 3 g/l |
| $KH_2PO_4$ | 2 g/l |
| $MgSO_4.7H_2O$ | 1 g/l |
| $ZnSO_4.7H_2O$ | 2.2 mg/l |
| pH | 7.0 |

EXAMPLE 1

3 l of a fermentation medium having the fundamental composition as shown above, with the addition of 1 g/l of adenine, was charged in a 7-l jar fermenter, and heated at 120° C. for 20 minutes. *Saccharomyces cerevisiae* P-154 was inoculated in the medium and subjected to aeration-agitation culture at 30° C. for 6 days (0.5 v.v.m., 400 rpm). 1.45 g/l of riboflavin was accumulated in the culture liquid obtained after cultivation.

700 ml portion of this culture liquid was cooled and centrifuged to precipitate a mixture of yeast cells and riboflavin crystals. 1 l of water was added to the precipitate, and extracted at 80° C. for 1.5 hour. After the heated liquid extract was cooled, 513 mg of riboflavin crystals having a purity of 93.5% were obtained. The crystals were recrystallized from dilute acetic acid, yielding riboflavin crystals of purity of 98% or more.

EXAMPLE 2

300 g of water was added to another 670 ml portion of the culture solution of Example 1, to which was further added hydrochloric acid to adjust the pH to 6.0. The solution was maintained at 80° C. for 1.5 hour and filtered under heating to obtain 850 g of a liquid extract. The liquid extract was concentrated 5 times and cooled to form 2.18 g of crude crystals containing riboflavin and calcium carbonate.

90 g of a 0.44% aqueous acetic acid solution was added to a 480 mg portion of these crude crystals. The solution was heated at 95° C. for 4 hours and, after filtering off the insoluble matters, the filtrate was cooled to yield 146 mg of riboflavin crystals having a purity of 99% or more.

EXAMPLE 3

*Saccharomyces cerevisiae* TW-573 was cultivated in the same manner as described in Example 1 except that the fermentation medium had the fundamental composition.

1.2 l of the culture (the amount of riboflavin being 1.47 g/l) was cooled and centrifuged to precipitate a mixture of yeast cells and riboflavin crystals. 2 l of water was added to the precipitate and extracted at 80° C. for 1.5 hours. The heated liquid extract was concentrated into a volume of 1 l and then cooled, yielding 895 mg of riboflavin crystals having a purity of 97.3%.

A 740 ml portion of the filtrate was further concentrated 3.3 times, yielding 388 mg of riboflavin crystals having a purity of 96.0%.

EXAMPLE 4

*Saccharomyces cerevisiae* P-154 was cultivated under shaking at 30° C. for 6 days in the same medium as used in Example 1. The amount of the riboflavin accumulated in the culture liquid was 1.55 g/l.

When *Saccharomyces cerevisiae* (*Candida robusta* AHU 3405), the parent strain of *Saccharomyces cerevisiae* P-154, was used for comparison, the amount of the riboflavin accumulated in the culture liquid was 0.85 g/l.

EXAMPLE 5

*Saccharomyces cerevisiae* P-154 was cultivated in the same manner as in Example 4, except that hypoxanthine was used in place of adenine in the same amount. The strain accumulated 1.48 g/l of riboflavin in the culture liquid.

EXAMPLE 6

*Saccharomyces cerevisiae* P-154 was subjected to liquid pre-cultivation in the same manner as in Example 4, and then cultivated under shaking at 30° C. for 6 days to prepare riboflavin, under the same conditions as in Example 4 except that ammonium sulfate was incorporated in the fermentation medium in an amount of 3.8 g/l and the concentration of zinc was varied as follows. The results are shown in Table 5.

TABLE 5

| Zinc concn. (mg/l) | Riboflavin (g/l) |
| --- | --- |
| 0 | 0.85 |
| 0.5 | 1.40 |
| 10 | 1.41 |
| 30 | 1.35 |

EXAMPLE 7

*Saccharomyces cerevisiae* TW-573 was cultivated under shaking at 30° C. for 9 days to prepare riboflavin in the fermentation medium having the same composition as that of Example 3 except that the amount of ammonium sulfate was 3.8 g/l and the zinc concentration was varied. The results are shown in Table 6.

TABLE 6

| Zinc concn. (mg/l) | Riboflavin (g/l) |
| --- | --- |
| 0 | 0.75 |
| 0.1 | 1.02 |
| 0.5 | 1.21 |
| 2.5 | 1.29 |
| 5 | 1.32 |
| 10 | 1.39 |
| 20 | 1.36 |
| 30 | 1.36 |
| 100 | 1.32 |

EXAMPLE 8

*Saccharomyces cerevisiae* TP-1010 was cultivated in the same manner as in Example 3, except that 0.1% of adenine was added to the fermentation medium of the fundamental composition. TP-1010 accumulated 2.50 g/l of riboflavin in the culture liquid.

EXAMPLE 9

*Saccharomyces cerevisiae* TP-1010 was subjected to liquid pre-cultivation in the same manner as in Example 3 and cultivated at 30° C. for 10 days to prepare riboflavin. The composition of the fermentation medium was the same as that of Example 8 except that the amount of ammonium sulfate was 3.8 g/l and the zinc concentration was varied. The results are shown in Table 7.

TABLE 7

| Zinc concn. (mg/l) | Riboflavin (g/l) |
| --- | --- |
| 0 | 1.62 |
| 0.5 | 2.17 |
| 2.5 | 2.18 |
| 5 | 2.26 |
| 10 | 2.20 |
| 30 | 2.22 |

EXAMPLE 10

*Saccharomyces cerevisiae* (*Candida robusta* AHU 3405) was inoculated on a potato dextrose agar medium (manufactured by Nissui Seiyaku) and cultured at 30° C. for 24 hours.

The grown yeast was inoculated in a liquid medium containing 2% of glucose, 0.5% of polypeptone, 0.3% of yeast extract, and 0.3% of malt extract, and subjected to rotation-shaking culture at 190 rpm at 30° C. for 25 hours. The pH value of the culture liquid was 4.3, and the absorbance at 610 nm was 5.7. The riboflavin-producing medium composition was 10.3% of calcium acetate as carbon source, 0.38% of ammonium sulfate, 0.2% of potassium dihydrogen phosphate, and 0.1% of magnesium sulfate and zinc sulfate was further added to the medium in an amount of 0.1 to 300 mg/l in terms of zinc ion concentration.

4.72 ml of this medium, the pH value being adjusted to 7.0, was charged in a test tube of 21 mm in diameter, whereto 0.28 ml of said pre-culture solution was inoculated and subjected to reciprocal shaking culture at 220 rpm at 30° C. for 8 days. The amount of the riboflavin in the culture liquid was calculated based on the absorbance of the centrifuged filtrate at 450 nm. The amount of the strain was determined based on the absorbance at 610 nm, and acetic acid was analyzed by means of high-performance liquid chromatography using an ion-exchange resin. As understood from the results shown in Table 8, the riboflavin productivity was remarkably increased by the addition of 0.1 to 100 mg/l of zinc. Similar results were obtained from another series of experiments in which the length of the cultivation days was varied. Those with marks a and b in Table 8 refer to part of those data, which were obtained after cultivation for 6.7 days (160 hours) and 4 days each.

TABLE 8

Effects of Zinc on the Production of Riboflavin

| $Zn^{++}$ concn. (mg/l) | riboflavin (g/l) | cell growth ($OD_{610\ nm}$) | residual acetic acid (g/l) |
|---|---|---|---|
| 0 | 0.46 | 14.8 | 5.7 |
| 0.1 | 0.92 | 11.6 | 3.4 |
| 0.2 | 1.00 | 10.3 | 2.2 |
| 0.3 | 0.98 | 9.5 | 7.3 |
| 0.4 | 1.01 | 8.6 | 5.7 |
| 0.5 | 0.99 | 9.0 | 9.9 |
| 0.75a | 0.75 | 11.3 | 6.7 |
| 1.0a | 0.83 | 11.4 | 6.5 |
| 3.0a | 0.79 | 11.3 | 6.6 |
| 6.0b | 0.78 | 16.9 | 0 |
| 10b | 0.78 | 17.3 | 0 |
| 30 | 0.80 | 8.0 | 25.2 |
| 100 | 0.77 | 7.5 | 29.4 |
| 300 | 0.31 | 3.9 | 65.3 |

EXAMPLE 11

Glucose, sucrose, glycerol, ethanol, and calcium gluconate were added in place of calcium acetate in Example 10. Calcium carbonate was added in an amount of 70% of the concentration of the carbon source in the case of the carbon sources except calcium gluconate to prevent the decrease in pH values. Biotin was also added to these carbon sources in an amount of 1 μg/l. As understood from Table 9, the effect of zinc was recognized with these carbon sources as well.

TABLE 9

Effects of Zinc with Various Carbon Sources

| Carbon source | Carbon source concn. (%) | $Zn^{++}$ concn. (mg/l) | riboflavin (mg/l) | cell growth ($OD_{610\ nm}$) |
|---|---|---|---|---|
| glucose | 7 | 0 | 58 | 19.1 |
|  | 7 | 0.5 | 116 | 10.0 |
|  | 1.75 | 0 | 11 | 9.5 |
|  | 1.75 | 0.5 | 51 | 6.3 |
| sucrose | 1.75 | 0 | 23 | 11.9 |
|  | 1.75 | 0.5 | 66 | 4.5 |
| glycerol | 1.75 | 0 | 19 | 15.7 |
|  | 1.75 | 0.5 | 36 | 10.8 |
| ethanol | 1.75 | 0 | 17 | 8.4 |
|  | 1.75 | 0.5 | 24 | 5.8 |
| calcium gluconate | 7 | 0 | 51 | 20.8 |
|  | 7 | 0.5 | 109 | 23.5 |

EXAMPLE 12

The examination was made on the effects of the addition of zinc ions in the presence of iron ions by cultivating the strains under the same conditions as in Example 10 except that ferrous sulfate was added to the riboflavin-producing medium in an amount of 5 mg/l in terms of iron ion concentration. As understood from Table 10, addition of zinc ion in an amount of 10 to 30 mg/l leads to satisfactory riboflavin production even in the presence of 5 mg/l of iron ions.

TABLE 10

Effects of Zinc in the Presence of Iron Ions

| $Fe^{++}$ (mg/l) | $Zn^{++}$ (mg/l) | riboflavin (g/l) | cell growth ($OD_{610\ nm}$) |
|---|---|---|---|
| 5 | 0 | 0.12 | 20.6 |
| 5 | 0.5 | 0.14 | 16.2 |
| 5 | 10 | 0.81 | 15.0 |
| 5 | 30 | 0.94 | 14.8 |
| 5 | 100 | 0.09 | 15.0 |
| 5 | 300 | 0.09 | 14.8 |

TABLE 10-continued

Effects of Zinc in the Presence of Iron Ions

| $Fe^{++}$ (mg/l) | $Zn^{++}$ (mg/l) | riboflavin (g/l) | cell growth ($OD_{610\ nm}$) |
|---|---|---|---|
| 0.1 or less | 0.5 | 0.95 | 16.5 |

EXAMPLE 13

*Saccharomyces cerevisiae* (*Candida robusta* AHU 3402) was subjected to the same experiment as described in Example 10. The amounts of riboflavin produced and cell growth after 6 days of cultivation are shown in Table 11. The effects of the addition of zinc was also recognized in the present strain.

TABLE 11

| $Zn^{++}$ (mg/l) | riboflavin (g/l) | cell growth ($OD_{610\ nm}$) |
|---|---|---|
| 0 | 0.32 | 19.9 |
| 0.5 | 0.51 | 19.3 |

What is claimed is:

1. A process for preparing riboflavin, which comprises:
   cultivating under aerobic conditions a riboflavin-producing culture medium containing (1) a microorganism having a riboflavin-producing ability and which is selected from the group consisting of *Saccharomyces cerevisiae* FERM BP-565, *Saccharomyces cerevisiae* FERM BP-566 and *Saccharomyces cerevisiae* FERM BP-567, (2) a carbon source and (3) a nitrogen source and (4) a purine compound when said microorganism is *Saccharomyces cerevisiae* FERM BP-565 or *Saccharomyces cerevisiae* FERM BP-566, to produce riboflavin in the culture medium; extracting riboflavin from the culture medium with hot water; and then crystallizing riboflavin from said hot water.

2. A process as claimed in claim 1, wherein said microorganism is *Saccharomyces cerevisiae* FERM BP-565 or *Saccharomyces cerevisiae* FERM BP-566 and said culture medium contains a purine compound.

3. A process for preparing riboflavin, which comprises: cultivating under aerobic conditions a culture medium containing (1) a microorganism having a riboflavin-producing ability and which is selected from the group consisting of *Saccharomyces cerevisiae* FERM BP-565, *Saccharomyces cerevisiae* FERM BP-566 and *Saccharomyces cerevisiae* FERM BP-567, (2) a $C_1$ to $C_4$ aliphatic compound as the sole carbon source, (3) a nitrogen source and (4) a purine compound when said microorganism is *Saccharomyces cerevisiae* FERM BP-565 or *Saccharomyces cerevisiae* FERM BP-566, to produce riboflavin in the culture medium; extracting riboflavin from the culture medium with hot water; and then crystallizing riboflavin from said hot water.

4. A process as claimed in claim 1, wherein said microorganism is *Saccharomyces cerevisiae* FERM BP-567 or *Saccharomyces cerevisiae* FERM BP-565.

5. A process as claimed in claim 1, wherein said microorganism is preliminarily cultivated to form a pre-cultured product and subsequently, said pre-cultured product is cultivated in said riboflavin-producing medium which also contains zinc ions.

6. A process as claimed in claim 2, wherein said microorganism is *Saccharomyces cerevisiae* FERM BP-566, and a compound selected from the group consisting of adenine, adenosine, adenylic acid, ribonucleic acid, hypoxanthine and inosine is added to said medium.

7. A process as claimed in claim 1, wherein said carbon source is selected from the group consisting of $C_1$ to $C_4$ aliphatic compounds, glucose, sucrose and xylose.

8. A process as claimed in claim 1, wherein said nitrogen source is selected from the group consisting of ammonium sulfate, ammonium chloride, ammonium carbonate and polypeptone.

9. A process as claimed in claim 1 in which the amount of riboflavin produced in the culture medium is at least 0.75 g/l.

10. A process for the preparation of riboflavin as set forth in claim (5), wherein the zinc concentration of said riboflavin-producing medium is not lower than 0.1 mg/l and not higher than 100 mg/l.

11. A process as set forth in claim (1), wherein acetic acid is said carbon source.

* * * * *